United States Patent [19]

Yung et al.

[11] Patent Number: 5,762,920
[45] Date of Patent: Jun. 9, 1998

[54] MEGAKARYOCYTE PRODUCTION

[75] Inventors: Yee Pang Yung, Canoga Park, Calif.; Karl Welte, Hanover, Germany

[73] Assignee: Amgen Inc., Thousand Oaks, Calif.

[21] Appl. No.: 571,746

[22] Filed: Dec. 13, 1995

Related U.S. Application Data

[63] Continuation of Ser. No. 268,864, Jun. 29, 1994, abandoned, which is a continuation of Ser. No. 967,914, Oct. 28, 1992, abandoned, which is a continuation of Ser. No. 444,888, Dec. 1, 1989, abandoned.

[51] Int. Cl.$^6$ .................................................. A61K 45/05
[52] U.S. Cl. ................................. 424/85.1; 424/85.2
[58] Field of Search .......................... 424/85.1, 85.2

[56] References Cited

U.S. PATENT DOCUMENTS

| | | | |
|---|---|---|---|
| 4,877,729 | 10/1989 | Clark et al. | 435/69.52 |
| 5,032,395 | 7/1991 | Clark et al. | 424/85.2 |
| 5,087,448 | 2/1992 | Burstein | 424/85.2 |

OTHER PUBLICATIONS

Tanikawa et al Exp. Hematol. (Sep. 1989) vol. 17, pp. 883–888.
Stedmans' Medical Dictionary, 24th Edition, p. 846.
Caracciolo et al., Blood, vol. 73(3), pp. 666–670, 1989 Feb.
Koike et al. (1988, Sep.) J. Exp. Med. 168:879–890.
Tanikawa et al. (1989, Sep.) Exp. Hematol. 17:883–888.
Rennick et al. (1989, May 15) Blood 73(7):1828–1835.
Ikebuchi et al. (1987) Proc. Natl. Acad. Sci. U.S.A. 84:9035–9039.
Wong et al. (1988, May 1) J. Immunology 140(9):3040–3044.
Lotem et al. (1989, Oct.) Blood 74(5):1545–1551.
Bagnara et al., Exp. Hematol. 15, 679–684 (1987).
Bruno et al., Exp. Hematol. 17, 1038–1043 (1989).
Cantrell et al., PNAS 82, 6250–6254 (1985).
Civin et al., J. of Immunol. 133, 147–153 (1984).
Clutterbuck et al. Blood. 71, 646–651 (1988).
Clutterbuck et al. Blood 73, 1504–1512 (1989).
Dukes et al. Megakaryocyte Development and Function, Alan R. Liss., New York, 1986, p. 105.
Fawcett et al. Exp. Hematol. 17, 25–29 (1989).
Gewirtz et al. J. of Immunol. 139, 2915–2924 (1987).
Geissler et al. J. of Immunol. 137, 2508–2513 (1986).
Geissler et al. Exp. Hematol. 15, 845–853 (1987).
Griffin et al. Blood 60, 30–37 (1982).
Hanson et al. Blood 70, 83–89 (1987).
Hirano et al. Nature 324, 73–76 (1986).
Hirano et al. J. Exp. Med. 166, 967–981 (1988).
Hoffman et al. J. Clin. Invest. 75, 1174–1182 (1985).
Hoffman et al. Blood. Cells. 13, 75–86 (1987).
Ishibashi et al. PNAS 86, 5953–5957 (1989).
Kanz et al. Blood 68, 991–995 (1986).
Kanz et al. Exp. Hematol. 16, 741–747 (1988).
Kawakita et al. British J. of Haematol. 52, 429–439 (1982).
Koike et al. Blood 75, 2286–2291 (1990).
Lea et al. Scand. J. of Immunol. 22, 207–216 (1985).
Levene et al. Exp. Hematol. 15, 181–189 (1987).
Long et al., J. Clin. Invest. 82, 1779–1786 (1988).
Lotem et al., Blood 74, 1545–1551 (1989).
Lu et al. Br. J. of Haematol. 70, 149–156 (1988).
McDonald et al., J. Lab. Clini. Med. 85, 59–66 (1975).
McNiece et al. Exp. Hemotl. 16, 807–810 (1988).
Mazur et al Blood 57, 277–286 (1981).
Mazur et al. Exp. Hematol. 15, 1128–1133 (1987).
Messner et al. J. Cell Physiol. Suppl 1, 45–51 (1982).
Metcalf et al. J. Cell. Physiol. 128, 421–431 (1986).
Nicola et al. J. of Biol. Chem. 258, 9017–9023 (1983).
Pelus et al. J. of Immunol. 140, 479–484 (1988).
Peschel et al. Blood 70, 254–263 (1987).
Petursson et al. Exp. Hematol. 16, 660–666 (1988).
Quesenberry et al. Blood 65, 214–217 (1985).
Rennick et al. Blood 73, 1828–1835 (1989).
Robinson et al. J. Clin. Invest. 79, 1648–1652 (1987).
Souza et al. Science 232, 61–65 (1986).
Sparrow et al. Leuk. Res. 11, 31–36 (1987).
Strath et al. J. of Immunol. Methods 83, 209–215 (1985).
Tanikawa et al. Exp. Hematol. 17, 883–888 (1989).
Tayrien et al. J. Biol. Chem. 262, 3262–3268 (1987).
Teramura et al. Exp. Hematol. 16, 843–848 (1988).
Vainchenker et al. Blood 54, 940—945 (1979).
Vainchenker et al. Blood 59, 514–521 (1982).
Warren et al. J. Immunol. 140, 94–99 (1988).
Warren et al. Exp. Hematol. 17, 1095–1099 (1989).
Williams et al. Blood 57, 157–163 (1981).
Williams et al. Leuk Res. 9, 1487–1496 (1985).
Wintrobe et al. Clinincal Hematology, 8th edition, pp. 1090–1127, 1981.
Yang et al. Cell 47, 3–10 (1986).
Yokota et al. PNAS 84, 7388–7392 (1987).

*Primary Examiner*—Chhaya D. Sayala
*Attorney, Agent, or Firm*—Robert B. Winter

[57] ABSTRACT

A method of increasing megakaryocyte production is disclosed. Such method comprises administering to a mammal a pharmaceutically effective amount of G-CSF and a pharmaceutically effective amount of IL-3 or GM-CSF, and optionally a pharmaceutically effective amount of IL-6. Another method comprises administering GM-CSF and IL-5. Also disclosed are compositions for use in increasing megakaryocyte production. A method of increasing blood platelet production is also disclosed. Such method comprises administering to a mammal a pharmaceutically effective amount of IL-6 and optionally a pharmaceutically effective amount of IL-3, G-CSF or GM-CSF. Also disclosed are compositions for use in increasing blood platelet production.

15 Claims, 10 Drawing Sheets

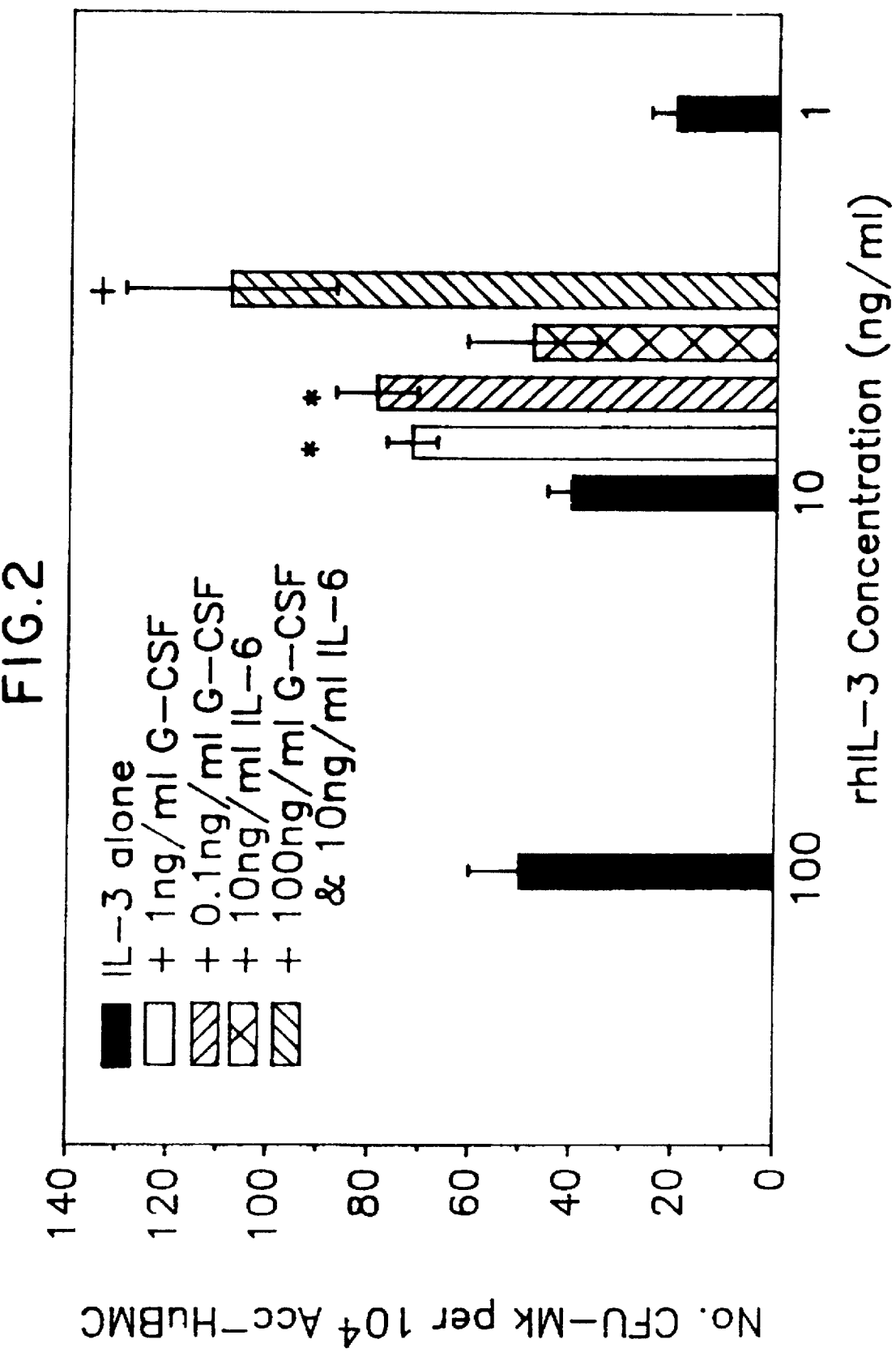

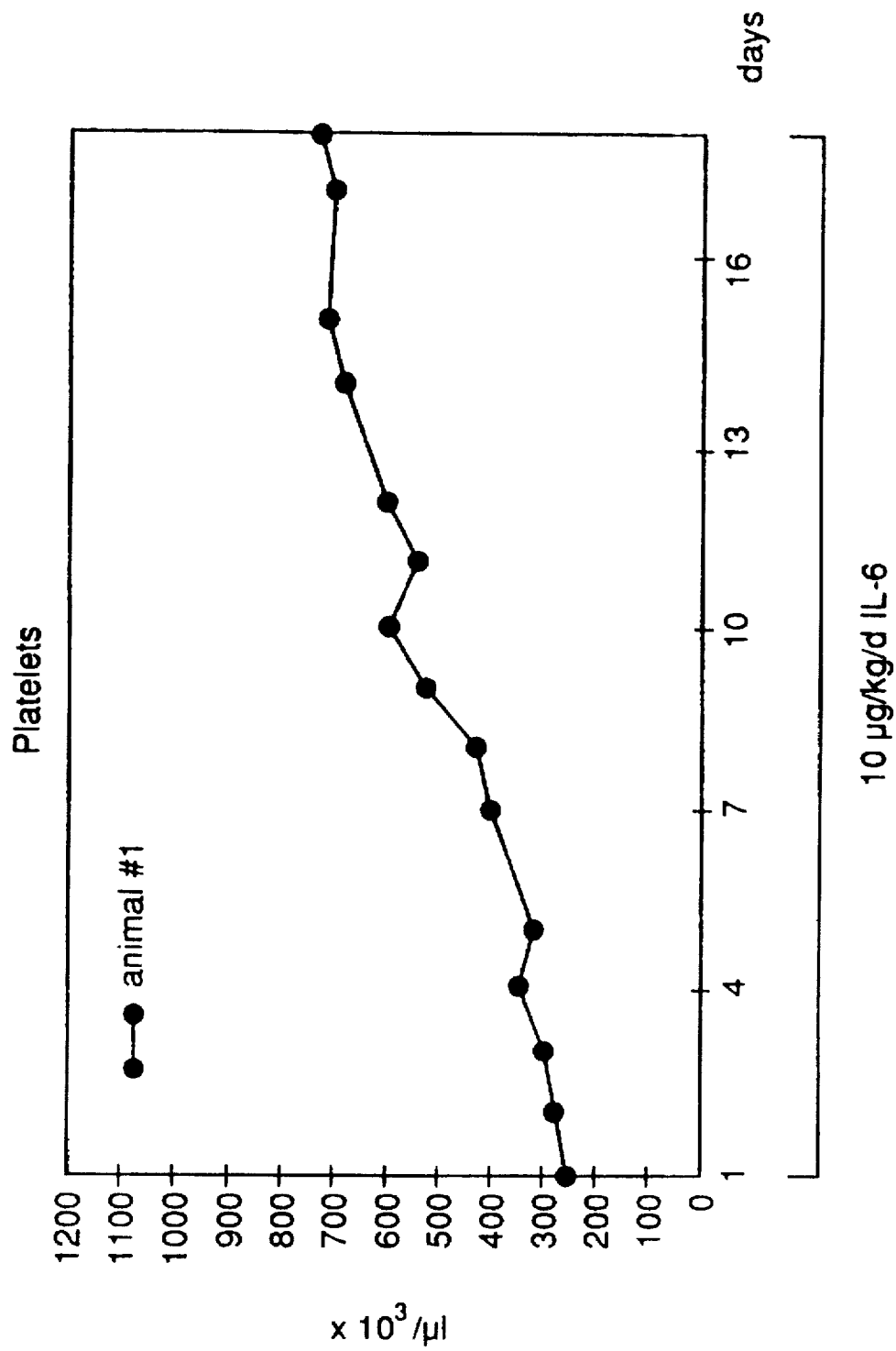

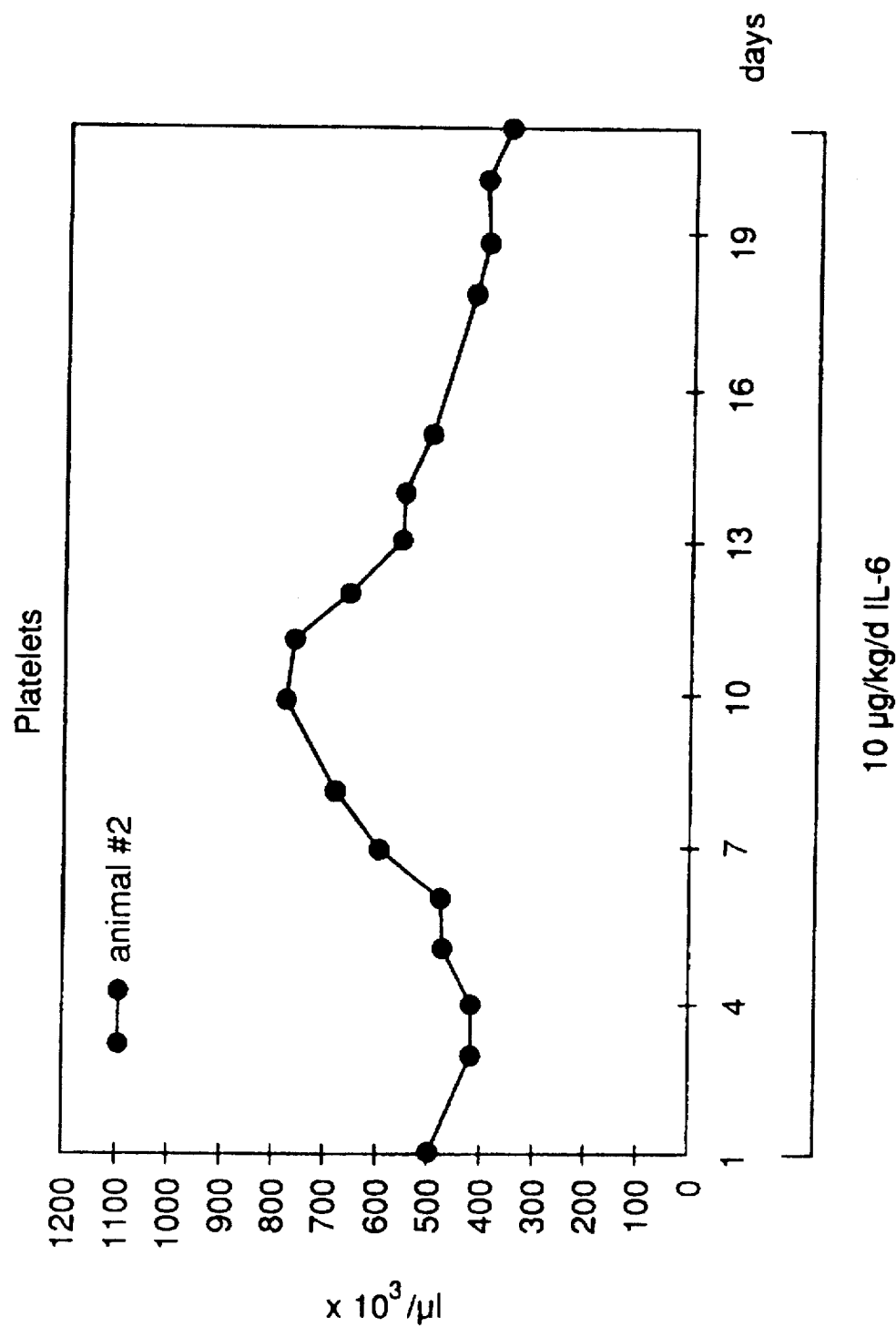

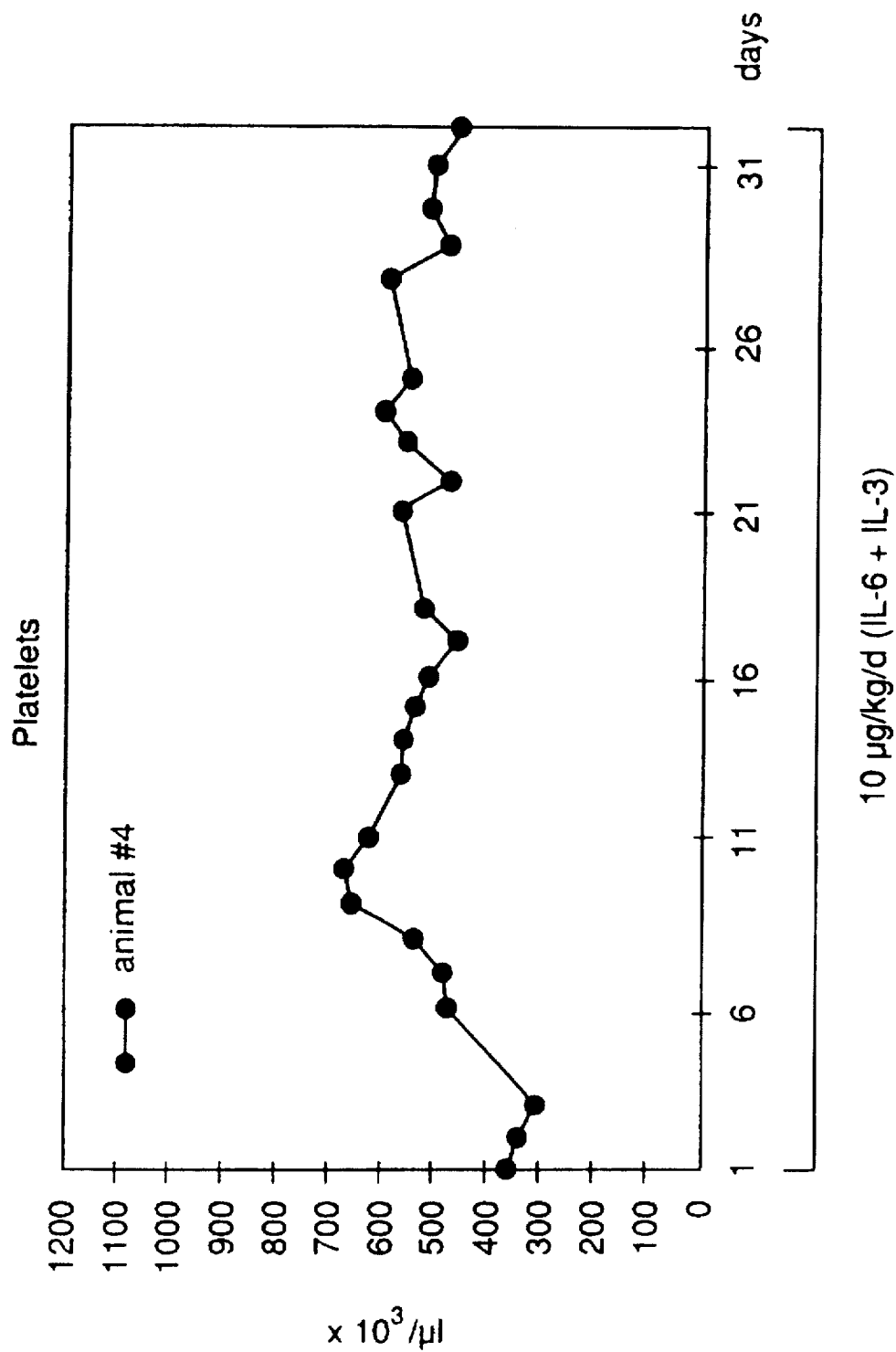

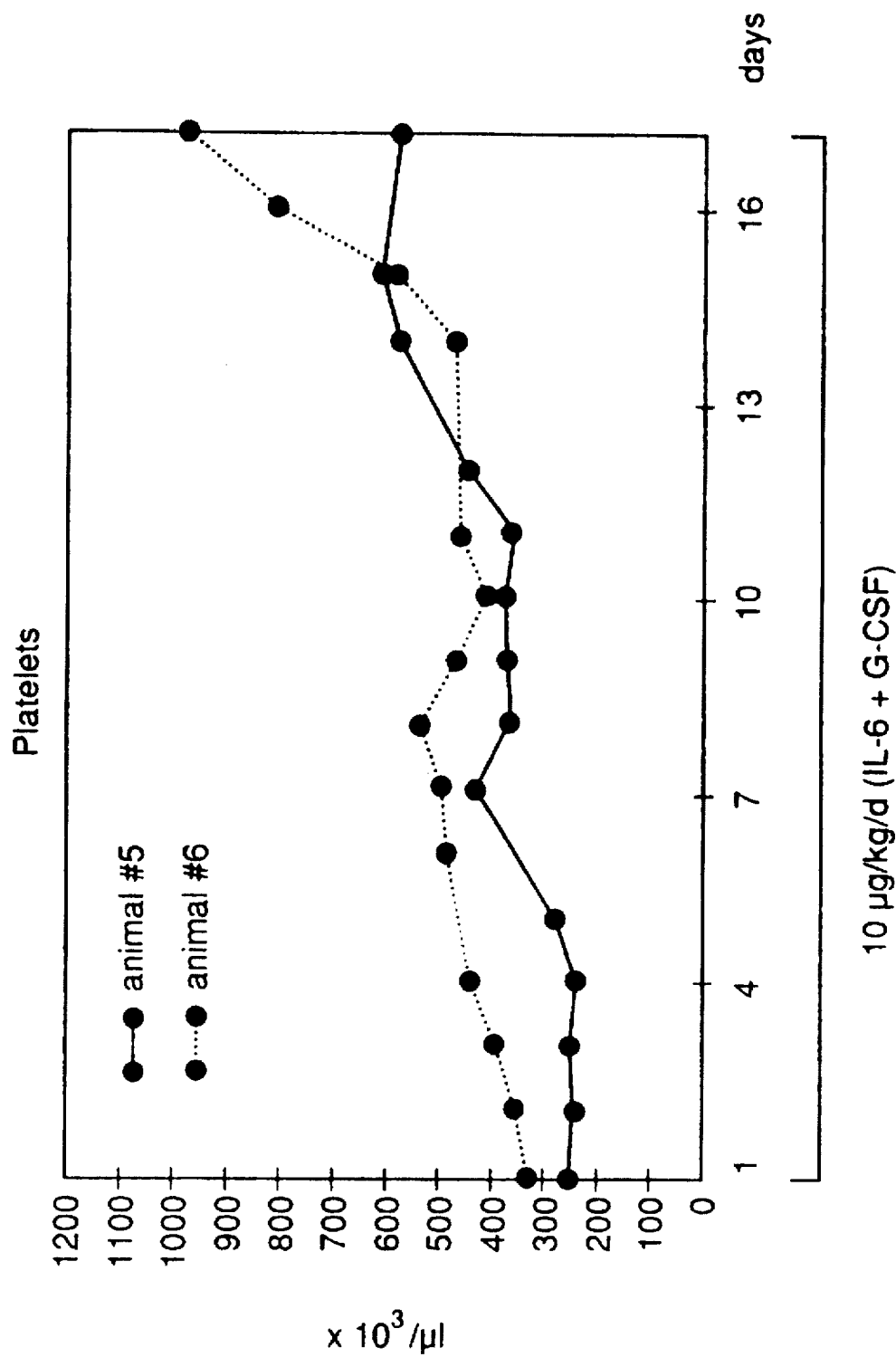

MEGAKARYOCYTE PRODUCTION

This application is a continuation of application Ser. No. 08/268,864 filed Jun. 29, 1994, which is a continuation of 07/967,914 filed Oct. 28, 1992, which is a continuation of application Ser. No. 07/444,888 filed Dec. 1, 1989, all now abandoned, which are incorporated herein by reference.

This invention is directed to methods of producing megakaryocytes and platelets. More particularly, the subject invention is directed to treatment of disorders involving megakaryocyte deficiency and low blood platelet counts.

BACKGROUND OF THE INVENTION

Megakaryocytopoiesis is the production of megakaryocytes. Megakaryocytes are large cells of the bone marrow which do not normally circulate in the blood. Mature megakaryocyte cells have a greatly lobulated nucleus, and mature blood platelets are released from the cytoplasm of the cells. Blood platelets (thrombocytes) which are chiefly known for their role in blood coagulation, lack a nucleus and DNA but contain active enzymes and mitochondria.

Studies with purified and recombinant hemopoietic factors in both human and murine systems have shown that granulocyte-macrophage colony stimulating factor (GM-CSF) and interleukin 3 (IL-3) are both capable of stimulating megakaryocyte (MK) colony formation from marrow or peripheral blood derived MK progenitor cells (CFU-MK) (1–7). GM-CSF and IL-3 stimulate mainly small MK colonies consisting of 5–20 cells (6–8). The ability of purified or recombinant GM-CSF or IL-3 to stimulate MK colony formation (1–7), and the additive effect of the two factors (3,6) is known. Granulocyte colony stimulating factor ("G-CSF") has been reported to enhance murine IL-3 dependent MK colony formation (8).

A megakaryocyte specific colony stimulating activity (MK-CSA) has been reported by a number of investigators to be present in peripheral blood leukocyte conditioned medium (PHA-LCM) (9,10), serum and plasma of various types of patients, in plasma of patients with amegakaryocytic thrombocytopenia (12) or urinary extracts from patients with aplastic anemia and idiopathic thrombocytopenia purpura (11), as well as from established cell sources (11–13). In addition, potentiating or synergistic factors that enhance MK colony number, size, cellularity and maturity have been described (8,14–16). The biochemical nature of MK-CSA and these auxiliary factors, however, have as yet not been well defined.

Tayrien and Rosenberg reported on a megakaryocyte stimulating factor (MSF) (13) and McDonald reported on the presence of a thrombopoietin (36), both present in medium conditioned by embryonic kidney cells. Thrombopoietin has been reported to lack direct MK colony stimulating activity (37). That MSF is a novel lineage specific MK-CSA with direct MK colony stimulating activity still awaits confirmation through gene cloning.

A requirement for two or more factors interacting to stimulate optimal in vitro MK colony formation in both the murine and human systems have been reported (14–16, 38). These studies implicate a potentiating activity for megakaryocytopoiesis, though the biochemical nature of the potentiating factor(s) remains to be determined. A number of investigators have reported on the ability of erythropoietin (EPO) to stimulate megakaryocyte colony formation (39,40) and to enhance MK cloning efficiency (41). Using highly enriched subpopulations of hematopoietic progenitor cells, and a serum depleted chemically defined medium, Lu et al. were unable to show a direct effect of EPO (6). Interleukin 4 (IL-4 or BSF-1), also reported to enhance murine MK colony formation (42) was equally ineffective.

SUMMARY OF THE INVENTION

The subject invention relates to a method of producing megakaryocytes. The invention comprises administering to a mammal a pharmaceutically effective amount of G-CSF and a pharmaceutically effective amount of IL-3 or GM-CSF, and optionally a pharmaceutically effective amount of IL-6. The invention also comprises administering a pharmaceutically effective amount of GM-CSF and a pharmaceutically effective amount of IL-5. The subject invention also relates to compositions comprising a pharmaceutically effective amount of G-CSF and a pharmaceutically effective amount of GM-CSF and/or IL-3 and optionally a pharmaceutically effective amount of IL-6, and compositions comprising a pharmaceutically effective amount of GM-CSF and a pharmaceutically effective amount of IL-5.

The subject invention relates to a method of producing blood platelets. The invention comprises administering to a mammal a pharmaceutically effective amount of IL-6 and optionally a pharmaceutically effective amount of IL-3, G-CSF or GM-CSF. The subject invention also relates to compositions comprising a pharmaceutically effective amount of IL-6 and a pharmaceutically effective amount of IL-3, G-CSF or GM-CSF.

BRIEF DESCRIPTION OF THE DRAWINGS

FIG. 2 shows synergistic enhancement of IL-3 dependent MK colony formation. Accessory depleted bone marrow cells were cultured at $10^4$/ml in triplicate plates. The symbol * represents values statistically significantly different (p<0.05) from that of IL-3 alone. The symbol + represents value statistically significantly different from that of IL-3+ G-CSF.

FIGS. 3A–3C show blood platelet counts in three monkeys receiving daily subcutaneous injections of IL-6 at 10 µg/kg for 18 days (animal #1) or 21 days (animal #2).

FIG. 4 shows blood platelet counts in one monkey receiving daily subcutaneous injections of IL-6 and IL-3 each at 10 µg/kg for 32 days.

FIG. 5 shows blood platelet counts in two monkeys receiving daily subcutaneous injections of IL-6 and G-CSF each at 10 µg/kg for 17 days (animal #5) or 25 days (animal #6).

DETAILED DESCRIPTION OF THE INVENTION

Figure 1:
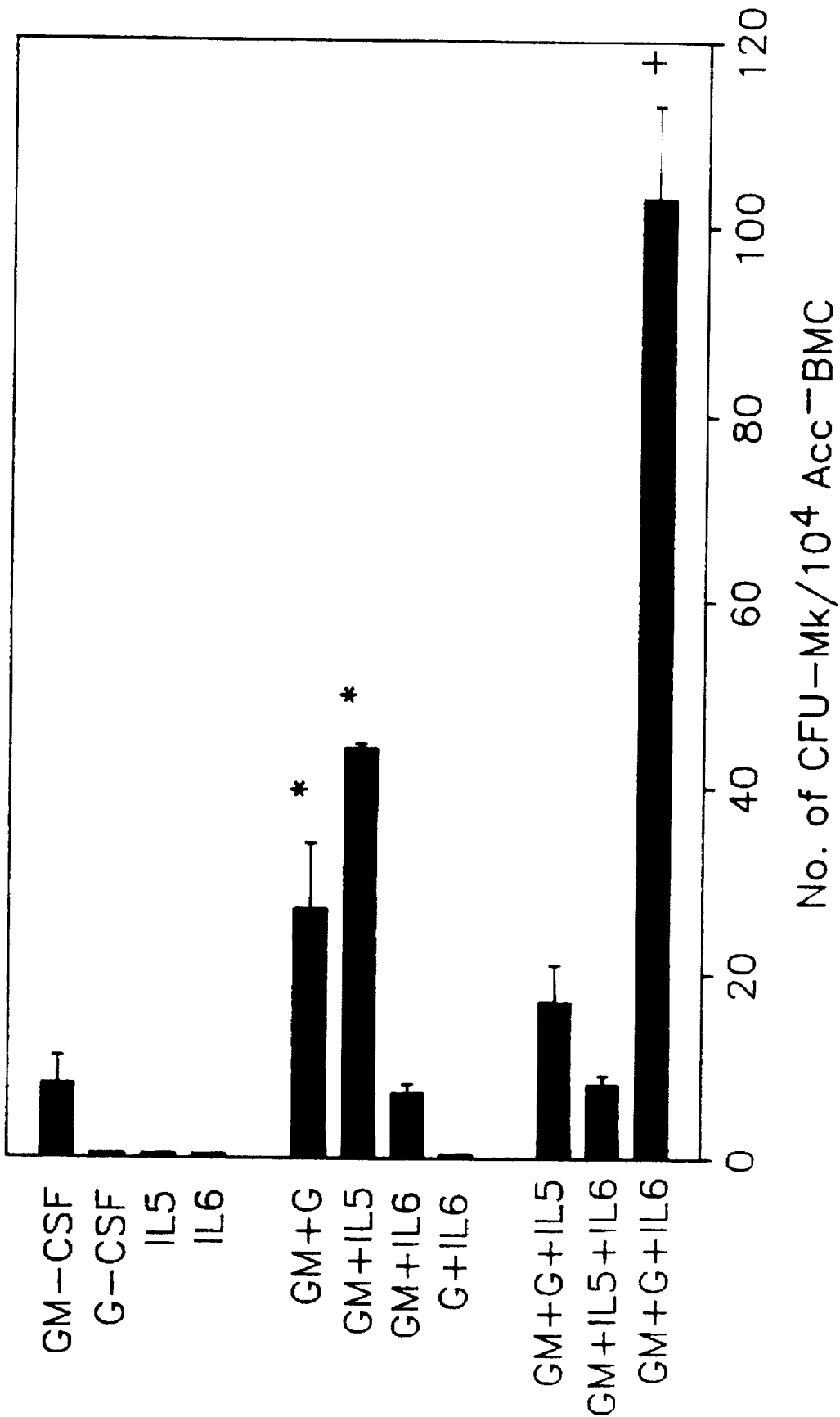
FIG. 1 shows synergistic enhancement of GM-CSF dependent MK colony formation. Accessory depleted bone marrow cells were cultured at $10^4$/ml in triplicate plates. GM-CSF and G-CSF were used at 1 ng/ml, and IL-5 and IL-6 at 10 ng/ml. The symbol * represents values statistically significantly different (p<0.05) from that of GM-CSF alone. The symbol+ represents values statistically significantly different from that of GM-CSF+ G-CSF.

According to the subject invention, methods for enhancing megakaryocytopoiesis are presented.

A semi-solid agarose clonal culture system independent of human serum or plasma was used to study the effect of various recombinant cytokines on human megakaryocytopoiesis. Since various studies have demonstrated regulatory influences of T cells, embryonic kidney cells and NK cells on in vitro megakaryocytopoiesis (13, 17–20), marrow cells exhaustively depleted of T cells, B cells, NK cells, macrophages, mature granulocytes and erythroid elements (21) were used as a source of enriched megakaryocyte precursors (CFU-MK). MK colonies were identified in situ by immuno-alkaline phosphatase staining for the MK/platelet specific markers platelet glyco-protein GPIIIa and/or Factor VIII related antigen (FVIII) (22–25). The examples below demonstrate a synergistic enhancement of GM-CSF/IL-3 dependent in vitro megakaryocytopoiesis by IL-5, G-CSF and IL-6.

Recombinant human granulocyte-macrophage colony stimulating factor (GM-CSF) (Cantrell et al., PNAS 82, 6250 (1985)) or interleukin 3 (IL-3) (Yang et al., Cell 47, 3 (1986)) both stimulated the formation of small MK colonies of between 3–20 cells in a dose dependent manner. Plateau levels of MK colonies were attained at concentrations of 0.1–1 ng/ml GM-CSF or approximately 1–10 ng/ml IL-3. These results are in keeping with those reported by others (5–7). The use of accessory depleted marrow cells and heat inactivated fetal bovine serum instead of human plasma minimized the effect of endogenously produced cytokines and accessory factors might be present in human plasma. Under such culture conditions, GM-CSF or IL-3 induced colonies were predominantly of small size (3–10 cells).

Recombinant human IL-5, (Yokota et al. PNAS 84, 7388 (1987)) and granulocyte colony stimulating factor (G-CSF) (Souza et al., Science 232, 61 (1986)) did not possess MK colony stimulating activity. However, the addition of either IL-5 or G-CSF to GM-CSF containing cultures resulted in an increase in total colony numbers as well as the appearance of larger sized colonies of up to 50 cells. G-CSF (at 0.01–1 ng/ml ), which by itself showed no MK colony stimulating activity, was found to significantly enhance MK colony formation induced by GM-CSF or IL-3, resulting in both increases in total colony number and cellularity. Recombinant IL-5 which, like G-CSF had no direct MK colony stimulating activity also showed an enhancing effect on GM-CSF dependent megakaryocytopoiesis. IL-5 did not synergize with G-CSF in augmenting GM-CSF induced MK colony formation. The effect of IL-5 on IL-3 induced MK colony formation is not presented since the combination of IL-3 and IL-5 results mainly in enhancement of eosinophil differentiation and colony formation (35).

While IL-6 (Hirano et al., Nature 324, 73(1986)) by itself failed to enhance GM-CSF dependent MK colony formation, it nevertheless was able to further augment the G-CSF enhancement of GM-CSF dependent MK colony formation. This enhancement was made by the simultaneous addition of IL-6 at 1–10 ng/ml. Moreover, the colonies stimulated by a combination of GM-CSF, G-CSF and IL-6 were generally larger in size with colonies of up to 50 cells or more readily detectable. Similar augmentation was observed with a combination of IL-3, G-CSF and IL-6. The enhancement of GM-CSF dependent MK colony formation by IL-5, however, could not be further augmented by IL-6. Time course studies showed G-CSF to be most effective when added together with GM-CSF or IL-3 at or shortly after the initiation of culture, whereas IL-6 appeared to augment the G-CSF induced enhancement when added as late as 7 days provided that G-CSF was present at the initiation of culture with GM-CSF or IL-3.

As used herein the terms "G-CSF", "GM-CSF", "IL-3", "IL-5", and "IL-6" denote proteins from natural source extraction and purification, or from recombinant cell culture systems. The terms likewise cover biologically active equivalents; e.g. differing in one or more amino acids in the overall sequence, or in glycosylation patterns. Further the terms are intended to cover substitution, deletion and insertion amino acid variants, or past translational modifications.

The subject invention also relates to compositions which comprise, consist essentially of, or consist of pharmaceutically effective amounts of G-CSF and GM-CSF or IL-3, and optionally IL-6. In another embodiment the invention relates to compositions which comprise, consist essentially of or consist of pharmaceutically effective amounts of GM-CSF and IL-5.

The subject invention relates to methods for enhancing thrombopoiesis. In order to analyze the in vivo effects of IL-6 alone and in combination with IL-3, GM-CSF and G-CSF on the hematopoietic system, the cynomolgus monkey was selected as a model system based upon similarities between simian and human hematopoiesis. IL-6 alone or in combination with IL-3, GM-CSF or G-CSF was administered on daily subcutaneous injections (10 μg/kg/d) over a varying time period. When IL-6 alone was administered, peripheral blood platelet counts increased two to three fold and reached a maximum by day 10 of treatment.

The subject invention also relates to compositions which comprise, consist essentially of, or consist of pharmaceutically effective amounts of IL-6 and optionally IL-3, G-CSF or GM-CSF.

Another embodiment of the subject invention is the addition of stem cell factor to any of the compositions or methods of treatment described herein. Stem cell factor is described in commonly owned U.S. patent application Ser. No. 422,383 hereby incorporated by reference.

Also comprehended by the invention are pharmaceutical compositions comprising pharmaceutically effective amounts of the proteins noted above together with suitable diluents, preservatives, solubilizers, emulsifiers, adjuvants and/or carriers.

Several variables will be taken into account by the ordinary artisan in determining the concentration of the proteins in the therapeutic compositions, and the dosages to be administered. Therapeutic variables also include the administration route, and the clinical condition of the patient.

The methods and composition of the subject invention are useful in treating thrombocytopenia, a condition marked by a subnormal number of platelets in the circulating blood and is the most common cause of abnormal bleeding. Thrombocytopenia results from three processes: (1) deficient platelet production, (2) accelerated platelet destruction, and (3) abnormal distribution of platelets within the body. A compilation of specific disorders related to thrombocytopenia is shown in Table A. Advantageous applications of the subject invention are to thrombocytopenia resulting from deficient platelet production and, in some cases, from accelerated platelet destruction.

TABLE A

Platelet Disorders

I. Deficient Platelet Production
  A. Hypoplasia or suppression of megakaryocytes Chemical and physical agents (ionizing radiation, antineoplastic drugs), aplastic anemia, congenital megakaryocytic hypoplasia myelophthisic processes, some viral infections
  B. Ineffective thrombopoiesis Disorders due to deficiency of vitamin $B_{12}$ or folic acid
  C. Disordered control mechanisms Deficiency of thrombopoietin, cyclic thrombocytopenia
  D. Miscellaneous Many hereditary forms II. Accelerated Platelet Destruction
  A. Due to immunologic processes Idiopathic Thrombocytopenia Purpura, drug-induced antibodies, various hemolytic anemia, fetomaternal incompatability, post-transfusion.
  B. Due to nonimmunologic processes Kasabach-Merritt syndrome, thrombotic thrombocytopenic purpura, infections (viral, bacterial, protozoan), massive transfusions III. Abnormal Platelet Distribution
  A. Disorders of the spleen
  B. Hypothermia anesthesia Deficient platelet production commonly results from hypoplasia or suppression of precursor megakarocytes. Depletion of megakaryocyte pools can occur during marrow injury caused by exposure to myelosuppressive drugs or irradation. Thus patients suffering from thrombocytopenia as a result of chemotherapy or radiation therapy can be treated by administration of pharmaceutically effective amounts of GM-CSF or IL-3 in combination with pharmaceutically effective amounts of G-CSF and IL-6 to raise blood platelet counts and prevent bleeding disorders. Depressed platelet levels may also result from ineffective thrombopoiesis or disorders related to thrombopietic control wherein megakaryocyte levels are normal but maturation of megakaryocytes has been disrupted. In these instances, an advantageous treatment method would be the administration of a pharmaceutically effective amount of IL-6 and optionally a pharmaceutically effective amount of IL-3, GM-CSF or G-CSF.

Accelerated platelet destruction can result in thrombocytopenia even though the production of megakaryocytes and platelets has not been diminished. Disorders such as idiophathic thrombocytopenic purpura (ITP) which are characterized by accelerated platelet destruction mediated by an autoimmune response can be treated by administration of immunosuppressants (such as corticosteroids) combined with a pharmaceutically effective amount of IL-6 and optionally a pharmaceutically effective amount of IL-3, GM-CSF or G-CSF.

GM-CSF and IL-3 play a primary role in the in vitro colony formation of human CFU-MK. The results presented below provide evidence for a regulatory role for human G-CSF, IL-5 and IL-6 in the in vitro GM-CSF or IL-3 dependent megakaryocyte colony formation. G-CSF, IL-5 and IL-6 increase cloning efficiency and colony size. The ability of IL-6 to augment the G-CSF enhancement of GM-CSF or IL-3 dependent MK colony formation further corroborate the existence of multifactorial as well as multilevel control mechanisms in human megakaryocytopoiesis. The results from the time course study below are suggestive of distinct mechanisms of action for G-CSF and IL-6. G-CSF appears to affect an early stage of megakaryocyte colony formation, possibly the induction of the self renewal of the MK precursors or the recruitment of earlier progenitors to differentiate, while IL-6 appears to affect a later event, perhaps by increasing colony size or induction of commitment toward the MK lineage.

The following examples are offered to more fully illustrate the invention, but are not to be construed as limiting the scope thereof.

EXAMPLE 1

Monoclonal antibodies and antisera

Monoclonal anti-Leu 1, Leu 5b, Leu 4, Leu 11b, Leu M1, Leu 16, Leu 19 were obtained from Becton Dickinson (Mountain View, Calif.), OKT4, OKT9, OKB2 from Ortho Diagnostic Systems (Raritan, N.J.), My4 and Mol from Coulter Immunology (Hialeah, Fla.), anti-glycophorin and IOT8 from AMAC, Inc. (Westbrook, Me.), monoclonal anti-GPIIIa, anti-Factor VIII related antigen (FVIII) and B22 from Dako (Santa Barbara, Calif.), and GPIIb/IIIa were obtained from Biodesign (Kennebunkport, Me.). A sheep anti-human albumin was purchased from Accurate Chemical (San Diego, Calif.). An affinity purified goat anti-mouse Ig and an alkaline phospatase conjugated $F(ab')_2$ fragment of affinity purified sheep anti-mouse IgG (containing 81.6 units of enzyme activity/ml) were purchased from Cappel/Organon Teknika Corp. (West Chester, Pa.). A sheep anti-human albumin was purchased from Serotech (Accurate Chemical). Goat anti-mouse IgG coated magnetic beads (Dynal) were purchased from Robbin Scientific (Mountain View, Calif.).

EXAMPLE 2

Recombinant growth factors

The specific activities of recombinant human G-CSF, GM-CSF and IL-3 used in the subject experiments were each approximately $10^8$ U/mg as assayed according to the procedure of Nicola et al. (26,27). Recombinant human IL-5 and IL-6 showed specific activities of $10^6$ U/mg, and $2\times10^7$ U/mg respectively with a unit of activity being defined as the reciprocal of the dilution yielding half maximal activity in their respective assay systems. IL-5 activity was assessed by eosinophil differentiation from human marrow eosinophil progenitors (28) and by the eosinophil peroxidase assay (29). IL-6 activity was assessed by measuring IgM production from the human B lymphoblastoid cell line, SKW6-CL4 (30).

EXAMPLE 3

Preparation of human bone marrow cells

Human bone marrow cells were obtained by iliac crest aspiration from healthy volunteer donors after informed consent. Buffy coat cells were separated from marrow by centrifugation on Ficoll-paque (density 1.077 g/ml; Pharmacia, Piscataway, N.J.) at 500×g for 30 min. Inter-face cells were collected and washed with phosphate buffered saline (PBS) containing 1% bovine serum albumin (BSA), and resuspended in Iscove's modified Dulbecco's medium (IMDM) supplemented with 10% heat inactivated fetal bovine serum (FBS). Marrow cells were depleted of adherent cells by adherence to plastic petri dishes for 90 min at 37° C. in a humidified 5% $CO_2$-95% air incubator. Unless otherwise stated, the marrow nonadherent low density (NAL) cells were treated with a monoclonal antibody mixture to deplete T cells (anti Leu 1, Leu 5b, OKT4, IOT8), B cells (anti-CD22, OKB2), NK cells (Leu 11b, Leu 19), residual monocytes, granulocytes and other differentiated myeloid cells (Leu M1, Mo1 , My4), erythroid elements (anti-glycophorin) and activated and proliferating cells (OKT9). In some experiments, only T cell depletion was carried out on the NAL cells. This was done by treatment with anti-Leu 1. Depletion of monoclonal antibody bound cells was accomplished by panning of goat anti-mouse IgG (50 µg/dish) coated petri dishes (Bectodishes, 100×5 mm, Fisher Scientific), followed by complement mediated lysis with 1:15 dilution of a Low-Tox rabbit complement (Accurate Chemical, Westbury, N.Y.) (31). To ensure exhaustive depletion of the antibody bound cells, the cell suspensions were further treated with 100 µl anti-Ig coated magnetic beads per $10^6$ cells for 20 min and the bound cells were removed by a magnet (32). The resultant populations were referred to as accessory depleted bone marrow cells (Acc⁻BMC) OR T depleted bone marrow cells (NALT-BMC). NALT-BMC constituted approximately 40% of the starting population, whereas Acc-BMC was approximately 5% of the starting population.

EXAMPLE 4
Clonal growth of megakaryocyte progenitors (CFU-MK) in agarose

Unless otherwise stated, Acc-BMC at $10^4$ cells per plate were cultured in 35 mm Lux petri dishes (Nunc, Inc.) in triplicates in 1 ml of 0.32% agarose in IMDM medium supplemented with 10% heat inactivated fetal bovine serum (Hyclone). Cultures were incubated at 37° C. in a 5% $CO_2$-95% air humidified incubator for 12 days.

EXAMPLE 5
Identification of megakaryocyte colonies

Megakaryocyte colonies were detected by a modification of the immuno-alkaline phosphatase technique described by Hanson et al. (34) using monoclonal antibodies against platelet glycoprotein GPIIIa or GPIIb/IIIa or factor VIII and alkaline phosphatase labeled F(ab')₂ fragment of the affinity purified sheep anti-mouse IgG (AP-anti-Ig). All antisera and monoclonal antibodies were diluted in PBS+1% bovine serum albumin (BSA). Culture plates were fixed with 2.5% formalin in acetone for 1 min, washed and transferred to Corning 75×50 mm microslides and air dried. The dried slides were soaked in water for 5–10 min to remove salts and color from the indicator present in culture medium. The slides were then air dried overnight, treated with PBS containing a 2% solution of human AB serum and 2% lamb serum to block nonspecific binding sites, followed by a 1:150 dilution of anti-GPIIIa or GPIIb/IIIa or anti-FVIII for 1 hr at 4° C., washed for 1 hr in a 1:1 diluted PBS. The slides were then treated for an hour at 4° C. with AP-anti-Ig at 1:250 dilution, followed by extensive washing with 1:1 diluted PBS to remove excess unbound antibodies. Controls were slides not treated with antibodies, or treated with the blocking antibody followed by AP-anti-Ig. Treated and control slides were then developed for 20–30 min in a freshly prepared mixture of 0.26 mg/ml α-naphthol AS-BI phosphate (solubilized in dimethyl formamide) and 1 mg/ml Fast Red TR salt in 0.2M Tris buffer (pH 9.0) containing 5 mM $MgCl_2$ and 1 mM Levamisole (all from Sigma) as an inhibitor of cellular alkaline phosphatase and counter stained for 5 min with Mayer's hematoxylin (Sigma). Megakaryocyte colonies positive for GPIIIa or FVIII show reddish cytoplasmic staining. Colonies on untreated and AP-anti-Ig treated slides gave no staining or weak background staining.

Results of triplicate cultures from single or multiple experiments were expressed as mean±standard deviation (x±S.D.). Statistical significance where indicated was determined using a two-tailed Student's t-test.

EXAMPLE 6
Enrichment of megakaryocyte progenitors by depletion of accessory cells The ability of NALT⁻ and Acc⁻ BMC to form megakaryocyte colonies in the presence of 1000 U/ml GM-CSF was assessed. The removal of T cells or accessory cells did not impair CFU-MK colony formation (Table 1).

TABLE 1

Enrichment of CFU-MK in marrow depleted of accessory cells

| Treatment of BMC | No. Cells Plated | No. CFU-MK ± SD* | Cloning efficiency(%) |
|---|---|---|---|
| NAL BMC | $10^5$ | 27 ± 2 | 0.03 ± 0.002 |
|  |  | 29 ± 1 | 0.03 ± 0.001 |
| NALT⁻ BMC | $5 \times 10^4$ | 46 ± 6 | 0.09 ± 0.012 |
|  |  | 25 ± 11 | 0.05 ± 0.022 |
|  |  | 53 ± 0 | 0.11 ± 0.000 |
| Acc⁻ BMC | $10^4$ | 46 ± 3 | 0.46 ± 0.03 + |
|  |  | 22 ± 2 | 0.22 ± 0.02 + |
|  |  | 25 ± 4 | 0.25 ± 0.04 + |
|  |  | 34 ± 6 | 0.34 ± 0.06 + |

*All cultures contain 10 ng (1000U) recombinant human GM-CSF per plate. Data represent the mean colony counts from triplicate cultures ± standard deviation. Results from separate experiments are listed.
+ Statistically significant compared to NAL MBC, p < 0.05.

T depletion which removed approximately 40% of marrow nucleated cells resulted in approximately a two fold increase in cloning efficiency, whereas accessory depletion which removed as much as 95% of the marrow nucleated cells resulted in a 10 fold or more increase in cloning efficiency.

A comparison of various cytokines showed that both GM-CSF and IL-3 possess MK colony stimulating activity, while G-CSF, IL-5 and IL-6 were inactive (Table 2).

TABLE 2

Effect of various recombinant hemopoietic factors on in vitro megakaryocyte colony formation*

|  | Concentration | No. Colonies ± SD (n) + | |
|---|---|---|---|
| Factor Added | ng/ml | Pool 1 | Pool 2 |
| None (Medium Control) | — | None | None |
| GM-CSF | 10 | 24 ± 3(3) | 49 ± 6 (2) |
|  | 1 | 14 ± 2(2) | 40 ± 10(10) |
|  | 0.1 | ND | 46 ± 6 (2) |
|  | 0.01 | ND | 10 ± 0 (1) |
| IL-3 | 100 | 12 ± 2(1) | 50 ± 10(1) |
|  | 10 | 14 ± 3(2) | 40 ± 5 (1) |
|  | 1 | ND | 20 ± 5 (1) |
| G-CSF | 1–10 | None (2) |  |
| IL-5 | 1–100 | None (2) |  |
| IL-6 | 1–10 | None (2) |  |

*Accessory depleted bone marrow cells were plated at $10^4$ cells/ml.
+ Results are expressed as mean colony number ± standard deviation (SD). n represents the number of experiments pooled. Some donor cells showed significantly higher response than others, hence these were pooled separately. ND, not determined.

G-CSF stimulated mainly neutrophil colonies, and IL-5 stimulated small numbers (generally less than 10) colonies of eosinophils (Luxol fast blue positive) whereas IL-6 at the concentrations tested had no detectable colony stimulating activity. GM-CSF stimulated MK colonies were generally of small size, mostly containing less than 10 cells per colony. IL-3 stimulated colonies tend to be slightly larger (5-20 cells). Immuno-alkaline phosphatase staining followed by Hematoxylin counter staining showed these MK colonies to be strongly positive for GPIIIa as well as FVIII and to have relatively high nuclear to cytoplasmic ratio (Plate 1). Control slides and non-MK colonies on the same slides showed no or very weak alkaline phosphatase staining (Plate 1). Concentrations of GM-CSF and IL-3 as low as 10 and 100 U/ml respectively were found to be adequate in stimulating plateau levels of MK colony growth. As different donors were used for each experiment, some differences in cloning efficiency among donors were observed. Some showed plateau levels of 10-20 colonies/$10^4$ Acc-BMC, while others were significantly higher (40-50 colonies). Hence, for clarity, the data were pooled separately (Pools 1&2, Table 2).

EXAMPLE 7

Enhancement of MK colony formation by G-CSF and IL-5

Although G-CSF by itself was inactive as a MK colony stimulating factor, it was nevertheless able to enhance the GM-CSF or IL-3 stimulated MK colony formation (Table 3).

TABLE 3

Enhancement of GM-CSF and IL-3 induced megakaryocyte colony formation by G-CSF and IL-5

| Factor(s) Added | No. Colonies ± SD* | | | |
|---|---|---|---|---|
| | Exp 1 | Exp 2 | Exp 3 | Exp 4 |
| GM-CSF (1 ng/ml) | 8 ± 3 | 13 ± 2 | 55 ± 1 | 149 ± 20 |
| GM-CSF (1 ng/ml) + G-CSF(0.01-1 ng/ml) | 27 ± 7 + | 21 ± 2 + | ND | 199 ± 23 + |
| GM-CSF (1 ng/ml) + IL-5(1-10 ng/ml) | 44 ± 0 + | 26 ± 3 + | ND | ND |
| GM-CSF (1 ng/ml) + IL-6(1-10 ng/ml) | 7 ± 1 | 14 ± 6 | 43 ± 4 | ND |
| IL-3 (10 ng/ml) | | | 40 ± 5 | |
| IL-3 (10 ng/ml) + G-CSF(0.1-1 ng/ml) | | | 76 ± 7 + | |
| IL-3 (10 ng/ml) + IL-6(10 ng/ml) | | | 48 ± 13 | |
| G-CSF (1 ng/ml) + IL-6(10 ng/ml) | None | None | | |
| IL-5 (10 ng/ml) + IL-6(10 ng/ml) | None | None | | |

*Accessory depleted bone marrow cells were plated at $10^4$ cells/ml. Results from separate experiments are expressed as mean colony counts of triplicate cultures ± standard deviation. In cases where a range of concentrations of G-CSF, IL-5 or IL-6 were indicated, the values shown represents the group means and standard deviations.
+ Statistically significant compared to GM-CSF or IL-3 controls, p < 0.05.

This enhancement could be detected irrespective of the baseline level of MK colony response to GM-CSF or IL-3. Thus, marrow cells that showed low or high numbers of MK colonies with GM-CSF or IL-3 showed corresponding enhancement with the addition of G-CSF (N.B. The high number of MK colonies with GM-CSF in Exp.4 was an isolated occurrence). In some experiments, the effect of IL-5 and IL-6 on GM-CSF or IL-3 dependent MK colony formation was also analyzed. Like G-CSF, IL-5 was found to enhance GM-CSF induced megakaryocytopoiesis. IL-6, on the other hand, was without direct enhancing effect on either GM-CSF or IL-3 dependent MK colony formation. Moreover, the enhancement by G-CSF and IL-5 was not limited to colony number. An increase in the frequency of colonies with 10 to 50 cells was also observed (Table 4).

TABLE 4

Effect of growth factors on megakaryocyte colony size distribution

| Growth Factor(s) Added | Percent* (x ± SD) of colonies with | | |
|---|---|---|---|
| | 3-10 cells | 10-50 cells | >50 cells |
| None | 0 | 0 | 0 |
| GM-CSF | 97 ± 4 | 1 ± 1 | 0 |
| GM-CSF + IL-5 | 80 ± 3 + | 20 ± 3 + | 0 |
| GM-CSF + G-CSF | 69 ± 6 + | 31 ± 6 + | 0 |
| GM-CSF + G-CSF + IL-6 | 29 ± 9 + | 68 ± 9 + | 3 ± 1 |
| IL-3 | 83 ± 1 | 16 ± 1 | 1 ± 1 |
| IL-3 + G-CSF | 71 ± 13 | 27 ± 13 | 2 ± 1 |
| IL-3 + G-CSF + IL-6 | 40 ± 1 | 49 ± 12 + | 11 ± 8 + |

*The percentages were obtained by counting all MK colonies on one plate. Data of randomly selected plates of each group from 2-4 experiments were pooled. GM-CSF, IL-3 and G-CSF were all used at 1 ng/ml while IL-5 and IL-6 were tested at 10 ng/ml in these experiments.
+ Statistically significant when compared to GM-CSF or IL-3 controls, p < 0.05.

EXAMPLE 8

Augmentation of G-CSF enhancement of MK colony formation by IL-6.

While IL-6 failed both to stimulate MK colony formation directly and to enhance GM-CSF and IL-3 stimulated MK colony formation, it nevertheless was able to further augment the G-CSF enhancement of MK colony formation (FIGS. 1 & 2). Thus, when IL-6 was added to cultures containing GM-CSF and G-CSF or IL-3 and G-CSF, a further increase in the number of MK colonies was observed. MK colony size was also increased, with the appearance of more MK colonies consisting of up to 50 cells or more (Table 4 and Plate 2a-f). This augmentation by IL-6 was specific for the G-CSF induced enhancement and its effect was not replicible with IL-5.

EXAMPLE 9

Time course of action of G-CSF and IL-6 augmentation of GM-CSF or IL-3 induction of MK colony formation.

To further analyse if G-CSF and IL-6 affect MK colony formation at the same stage or at different stages, a time course study was carried out. As can be seen in Table 5, the G-CSF enhancement of GM-CSF or IL-3 induced MK colony formation was optimal when both factors were present early on (no later than day 3) in the culture period.

TABLE 5

Time Course of Effect of G-CSF and IL-6

| Time of Addition of | | | No. CFU-Mk per $10^4$ Acc-BMC | | |
|---|---|---|---|---|---|
| GM-CSF/IL-3 | G-CSF | IL-6 | Exp. 1 | Exp. 2 | Exp. 3§ |
| d0 | None | None | 9 ± 2 | 30 ± 4 | 17 ± 5 |
| d0 | d0 | None | 19 ± 3* | 74 ± 4* | 49 ± 6* |
| d0 | d3 | None | 15 ± 6 | 75 ± 9* | 44 ± 5* |
| d0 | d5 | None | 15 ± 5 | 69 ± 27 | 39 ± 8* |
| d0 | d7 | None | 7 ± 1 | 37 ± 6 | 27 ± 1 |
| d0 | d0 | d0 | 29 ± 3 + | 134 ± 6 + | 74 ± 4 + |
| d0 | d3 | d3 | 31 ± 4 | 130 ± 8 + | 62 ± 2 |
| d0 | d5 | d5 | 6 ± 2 | 35 ± 0 | 29 ± 1 |
| d0 | d7 | d7 | 3 ± 1 | 39 ± 5 | 21 ± 6 |

TABLE 5-continued

Time Course of Effect of G-CSF and IL-6

| Time of Addition of | | | No. CFU-Mk per $10^4$ Acc-BMC | | |
|---|---|---|---|---|---|
| GM-CSF/IL-3 | G-CSF | IL-6 | Exp. 1 | Exp. 2 | Exp. 3§ |
| d0 | d0 | d3 | 32 ± 5 + | 102 ± 7 + | 76 ± 6 + |
| d0 | d0 | d5 | 27 ± 7 | 99 ± 10 + | 83 ± 10 + |
| d0 | d0 | d7 | 33 ± 3 + | 91 ± 4 + | 92 ± 0 + |

§In Exp. 3, IL-3 was used instead of GM-CSF, GM-CSF, G-CSF and IL-3 were all used at 1 ng/ml, whereas, IL-6 was used at 10 ng/ml in these experiments.
*Statistically significantly different (p < 0.05) when compared to results of GM-CSF or IL-3 alone.
+ Statistically significantly different from the corresponding results with Gm-CSF + G-CSF or Il-3 + G-CSF.

Likewise, the synergistic effect of G-CSF and IL-6 was observed only when both factors were added together with GM-CSF or IL-3 at the initiation of culture or no later than 3 days afterwards. However, when G-CSF was present at the initiation of culture with GM-CSF or IL-3, then the IL-6 induced augmentation could be observed even when IL-6 was added as late as 5–7 days.

EXAMPLE 10

In vivo effects of IL-6 on hematopoiesis.

Juvenile healthy female cynomolgus monkeys (Macaque fasicularis) were obtained from Tierlaboratorium, Universitat Dusseldorf, FRG. They were maintained according to the German guidelines for the use and care of laboratory animals. Blood samples were taken by puncture of peripheral veins. Prior to all manipulations, animals were anesthetized with ketamine hydrochloride (Hersteller).

Hematologic counts were performed by an automated hematologic analyzer. Differential counts of leukocytes were performed on slides stained with May-Gruenwald-Giemsa.

Figure 3C:
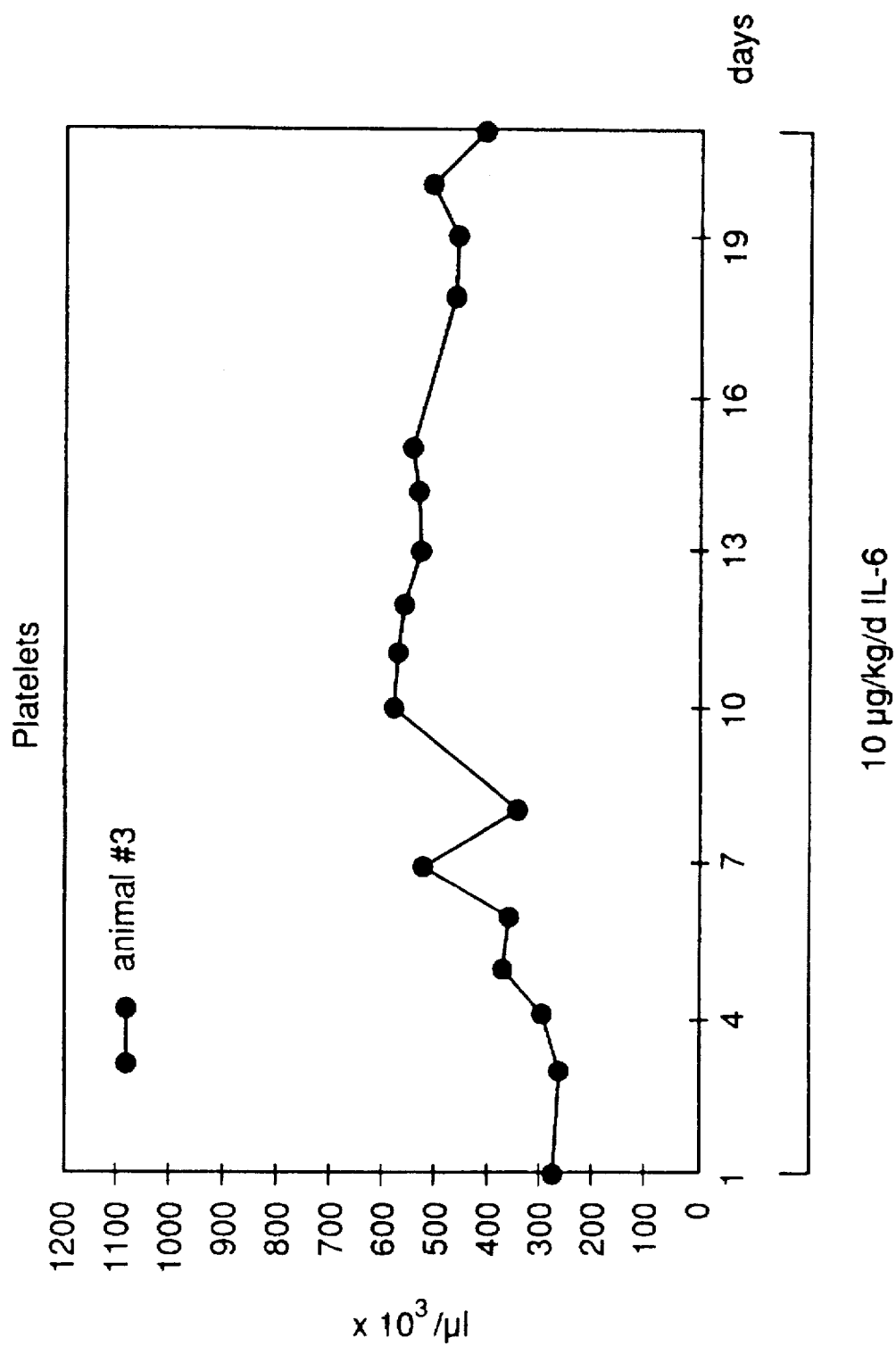

To assess the biological activity of IL-6 on platelet production, daily subcutaneous injections of IL-6 at 10 ug/kg/d were given to three healthy monkeys. The peripheral blood platelet counts were measured daily and are shown in FIG. 3. Animal #1 received IL-6 from day 1 to day 18, animals #2 and #3 from day 1 to day 21. In all three monkeys the platelet counts (cells per ul) increased significantly, in animal #1 from 254,000 to 756,000; in animal #2 from 513,000 to 786,000; in animal #3 from 276,000 to 592,000. IL-6 did not significantly change the number of peripheral blood neutrophils, eosinophils, basophils, lymphocytes and erythrocytes.

IL-6 and IL-3 were administered simultaneously as daily subcutaneous injections to one monkey, 10 ug/kg/d each, to investigate the in vivo effects of this combination. Levels of peripheral blood platelets in animal #4, which had been treated from day 1 to day 32, are shown in FIG. 4. In combination with IL-3, IL-6 led to an increase of peripheral blood platelets from 362,000 to a maximum of 675,000 on day 10 of the treatment. This increase is equivalent to that seen with IL-6 alone. The combination of IL-6 and IL-3 significantly increased eosinophil counts from 214 to a maximum of 4,089 and basophil counts from initially 0 to a maximum of 2,240 . Levels of other blood cells, such as neutrophils, monocytes, lymphocytes and erythrocytes did not change significantly.

Two monkeys were treated with the combination of IL-6 and G-CSF, each 10 ug/kg/d subcutaneously, over a time period of 17 days in animal #5 and 25 days in animal #6. In animal #5 the peripheral blood platelet counts increased from 252,000 to a maximum of 638,000; in animal #6 from 342,000 to a maximum of 1,104,000. These results are shown in FIG. 5. Neutrophils increased from 1,624 to a maximum of 33,947 (for animal #5) and from 5,060 to 52,809 (for animal 6). Lymphocytes increased from 3,864 on day 1 to a maximum of 9,693 (for animal #5) and from 5,500 to a maximum of 16,628 (for animal #6). There was no significant change in the levels of the other peripheral blood cells.

Figure 6:
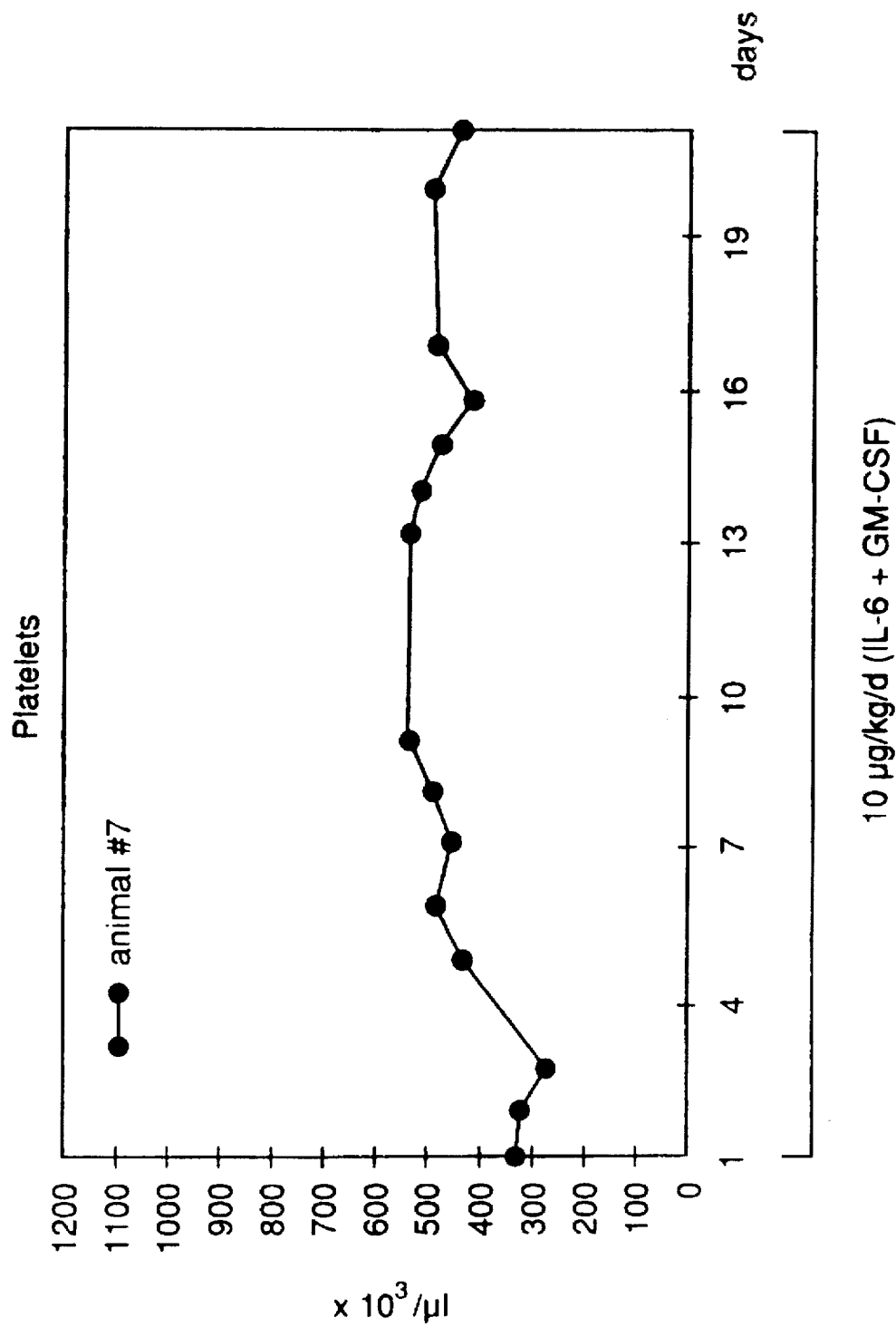
FIG. 6 shows blood platelet counts in one monkey receiving daily subcutaneous injections of IL-6 and GM-CSF each at 10 µg/kg for 21 days.
Figure 7A:
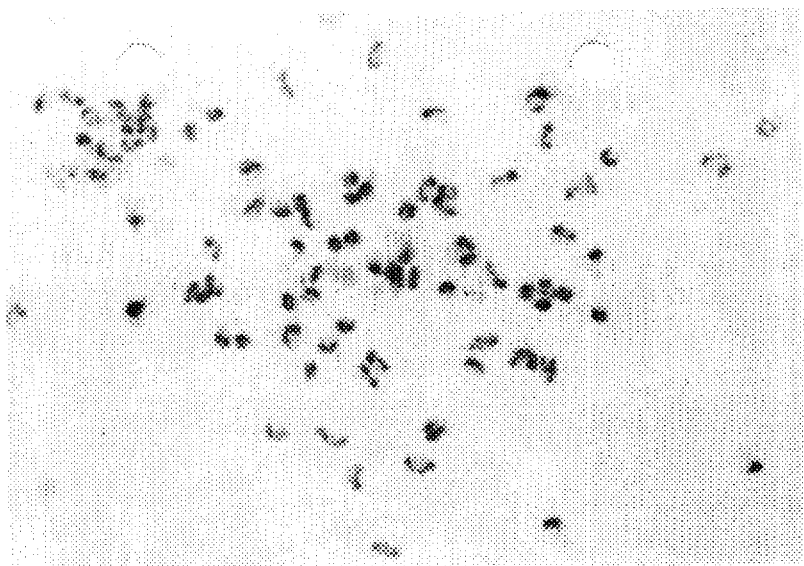
FIGS. 7A–7C show immuno-alkaline phosphatase negative granulocyte-macrophage colonies (400×) (FIGS. 7A & 7B). Low magnification (100×) view to show 2 immuno-alkaline phosphatase positive MK colonies among immuno-alkaline phosphatase negative GM colonies (FIG. 7C). A monoclonal murine anti-human GPIIIa antibody was used in these preparations. Use of anti-FVIII gave similar results.
Figure 7B:
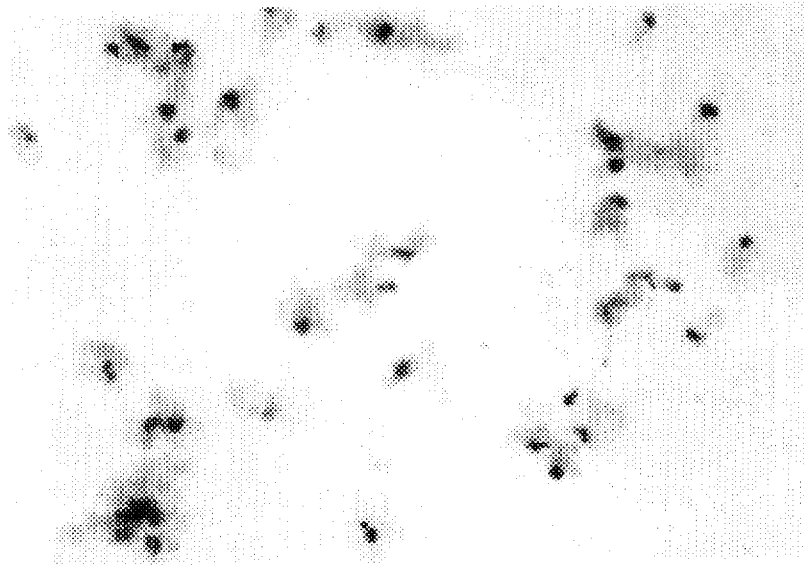
Figure 7C:
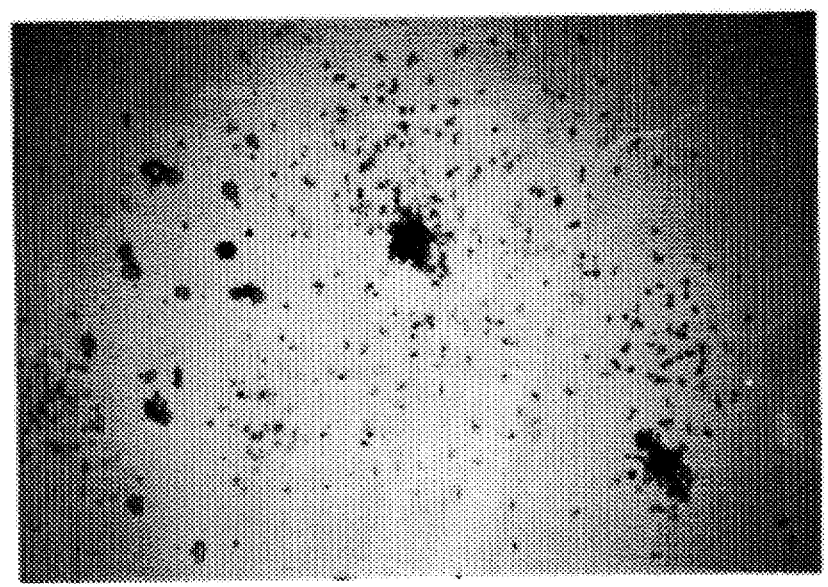
Figure 8A:
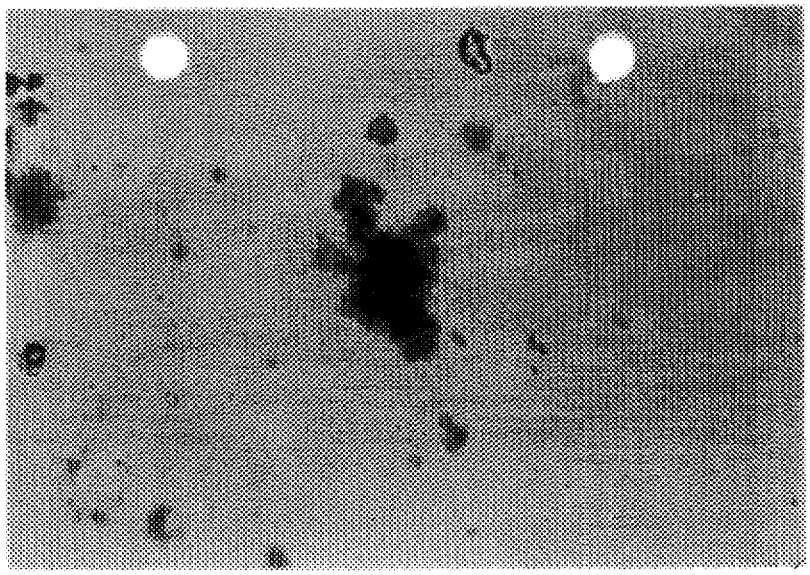
FIGS. 8A–8C show small immuno-AP positive MK colony (400×) (8A). Medium sized strongly immuno-AP positive MK colony, high magnification (1000×) (FIG. 8B). Large strongly immuno-AP positive MK colony (400×) (FIG. 8C). A monoclonal murine anti-human GPIIIa was used as the primary antibody in these preparations. The use of anti-FVIII yielded similar results.
Figure 8B:
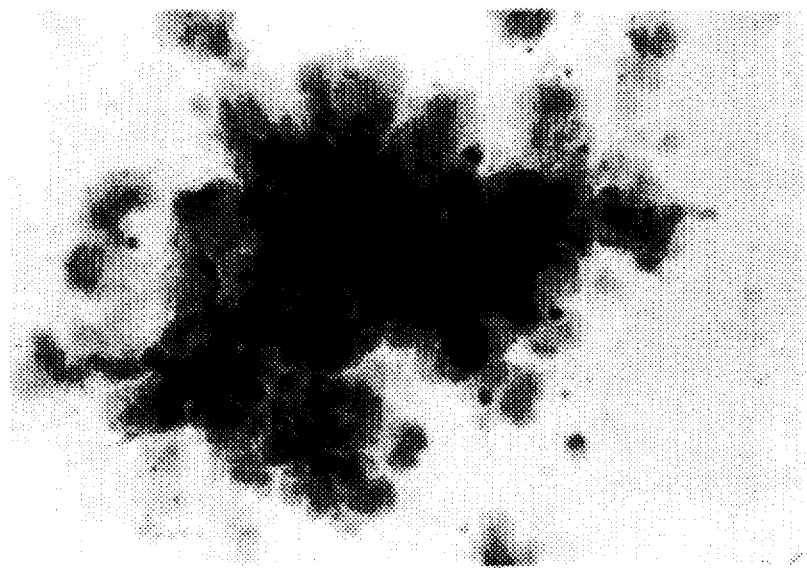
Figure 8C:
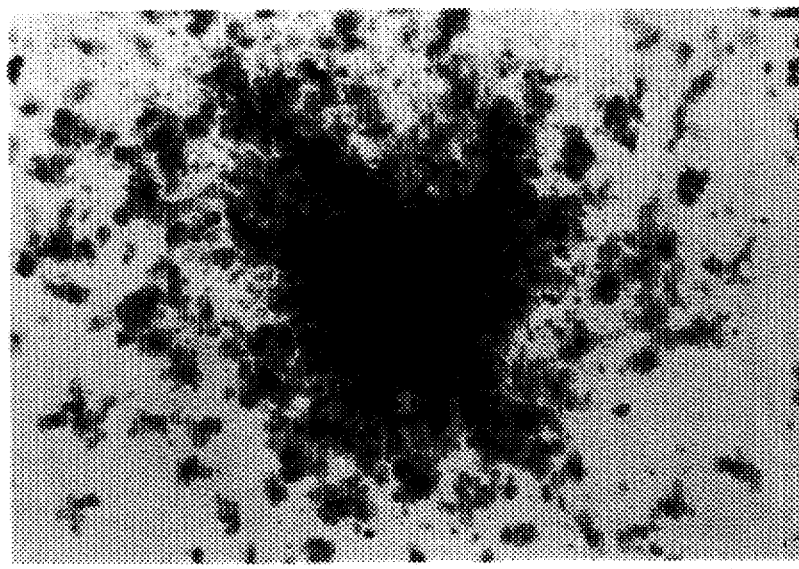

Animal #7 has been treated with a combination of IL-6 and GM-CSF as described above from day 1 to day 21. Platelet counts increased from 334,000 initially to a maximum of 538,000 as shown in FIG. 6. Neutrophil counts rose significantly from 2,652 to a maximum of 34,286, eosinophil counts increased from 156 to 4,704, and lymphocyte counts increased from 12,480 to 16,800. There was no significant change in the levels of basophils and monocytes.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

REFERENCES

1. Williams N., Sparrow R., Gill K., Yasmeen D., McNiece I.: Murine megakaryocyte colony stimulating factor: its relationship to interleukin-3. Leuk. Res. 9:1487, 1985.
2. Quesenberry P. J., Ihle J. N., McGrath E.: The effect of interleukin-3 and GM-CSA-2 on megakaryocyte and myeloid clonal colony formation. Blood 65:214, 1985.
3. Robinson B. E., McGrath H. E., Quesenberry P. J.: Recombinant murine granulocyte-macrophage colony stimulating factor has megakaryocyte colony stimulating activity and augments megakaryocyte colony stimulation by interleukin-3. J. Clin. Invest. 79:1648, 1987.
4. Metcalf D., Burgess A. W., Johnson G. R., Nicola N. A., Nice E. C., DeLamarter J., Thatcher D. R., Mermod J. J.: In vitro actions on hemopoietic cells of recombinant murine GM-CSF purified after production in Escherichia coli: Comparison with purified native GM-CSF. J. Cell Physiol. 128:421, 1986.
5. Mazur E. M., Cohen J. L., Wong G. G., Clark S. C.: Modest stimulatory effect of recombinant human GM-CSF on colony growth from peripheral blood human megakaryocyte progenitor cells. Exp. Hematol. 15:1128, 1987.
6. Lu L., Briddell R. A., Graham C. D., Brandt J. E., Bruno E., Hoffman R.: Effect of recombinant and purified human haematopoietic growth factors on in vitro colony formation by enriched populations of human megakaryocyte progenitor cells. Br. J. Haematol. 70:149, 188.
7. Teramura M., Katahira J., Hoshino S., Motoji T., Oshimi K., Mizoguchi H.: Clonal growth of human megakaryocyte progenitors in serum-free cultures: Effect of recombinant human interleukin 3. Exp. Hematol. 16:843, 1988.
8. McNiece I., McGrath H. E., Quesenberry P. J.: Granulocyte colony stimulating factor augments in vitro megakaryocyte colony formation by interleukin-3. Exp. Hematol. 16:807, 1988.
9. Messner H. A., Jamal N., Izaguirre C.: The growth of large megakaryocyte colonies from human bone marrow. J. Cell Physiol. Suppl. 1:45, 1982.
10. Bagnara, G. P., Guarini A., Gaggioli L., Zauli G., Catani L., Valvassori L., Zunica G., Gugliotta L., Marini M.: Human T-lymphocyte-derived megakaryocyte colony-stimulating activity. Exp. Hematol. 15:679, 1987.

11. Kawakita M., Miyake T., Kishimoto S., Ogawa M.: Apparent heterogeneity of human megakaryocyte colony- and thrombopoiesis-stimulating factors: studies on urinary extracts from patients with aplastic anaemia and idiopathic thrombocytopenic purpura. Br. J. Haematol. 52:429, 1982.

12. Hoffman R., Yang H. H., Bruno E., Stravena J. E.: Purification and partial characterization of a megakaryocyte colony-stimulating factor from human plasma. J. Clin. Invest. 75:1174, 1985.

13. Tayrien G., Rosenberg R. D.: Purification and properties of a megakaryocyte stimulatory factor present both in the serum-free conditioned medium of human embryonic kidney cells and in thrombocytopenic plasma. J. Bio. Chem. 262:3262, 1987.

14. Long M. W., Hutchinson R. J., Gragowski L. L., Heffner C. H., Emerson S. G.: Synergistic regulation of human megakaryocyte development. J. Clin. Invest. 82:1779, 1988.

15. Williams N., Jackson H., Ralph P., Nakoinz I.: Cell interactions influencing murine marrow megakaryocytes: Nature of the potentiator cell in bone marrow. Blood 57:157, 1981.

16. Fawcett J., Huat O. S., Williams N.: The role of factors from lung in murine megakaryocytopoiesis. Exp. Hematol. 17:25, 1989.

17. Giessler D., Lu L., Bruno E., Yang H. H., Broxmeyer H. E., and Hoffman R.: The influence of T lymphocyte subsets and humoral factors on colony formation by human bone marrow and blood megakaryocyte progenitor cells in vitro. J. Immunol. 137:2508, 1986.

18. Kanz L., Lohr G. W., Fauser A. A.: Lymphokine(s) from isolated T lymphocyte subpopulations support multilineage hematopoietic colony and megakaryocytic colony formation. Blood 68:991, 1986.

19. Giessler D., Konwalinka G., Peschel C., Braunsteiner H.: The role of erythropoietin, megakaryocyte colony-stimulating factor, and T-cell-derived factors on human megakaryocyte colony formation: Evidence for T-cell-mediated and T-cell-independent stem cell proliferation. Exp. Hematol. 15:845, 1987.

20. Gewirtz A. M., Xu W. Y., Mangan K. F.: Role of natural killer cells, in comparison with T lymphocytes and monocytes, in the regulation of normal human megakaryocytopoiesis in vitro. J. Immunol. 139:2915, 1987.

21. Griffin J. D., Beveridge R. P., Schlossman S. F.: Isolation of myeloid progenitor cells from peripheral blood of chronic myelogenous leukemia patients. Blood 60:30, 1982.

22. Mazur E. M., Hoffman R., Chasis J., Marchesi S., Bruno E.: Immunofluorescent identification of human megakaryocyte colonies using an antiplatelet glycoprotein antiserum. Blood 57:277, 1981.

23. Vainchenker W., Deschamps J. F., Bastin J. M., Guichard J., Titeux M., Breton-Gorius J., McMichael A. J.: Two monoclonal antiplatelet antibodies as markers of human megakaryocyte maturation: Immunofluorescent staining and platelet peroxidase detection in megakaryocyte colonies and in in vivo cells from normal and leukemic patients. Blood 59:514, 1982.

24. Levene R. B., Williams N. T., Lamaziere J. M. D., Rabellino E. M.: Human megakaryocytes. IV. Growth and characterization of clonal megakaryocyte progenitors in agar. Exp. Hematol. 15:181, 1987.

25. Kanz L., Mielke R., Fauser A. A.: Analysis of human hemopoietic progenitor cells for the expression of glycoprotein IIIa. Exp. Hematol. 16:741, 1988.

26. Nicola N. A., Metcalf D., Matsumoto M., Johnson G. R.: Purification of a factor inducing differentiation in murine myelomonocytic leukemia cells. J. Biol. Chem. 258:9017, 1983.

27. Souza L. M., Boone T. C., Gabrilove J., Lai P. H., Zsebo K. M., Murdock D. C., Chazin V. R., Bruszewski J., Lu H., Chen K. K., Barendt J., Platzer E., Moore M. A. S., Mertelsmann R., Welte K.: Recombinant human granulocyte colony stimulating factor: Effects on normal and leukemic myeloid cells. Science 232:61, 1986.

28. Clutterbuck E., Sanderson C. J.: Human eosinophil hematopoiesis studied in vitro by means of murine eosinophil differentiation factor (IL-5): production of functionally active eosinophils from normal human bone marrow. Blood 71:646, 1988.

29. Strath M., Warren D. J., Sanderson C. J.: Detection of eosinophils using an eosinophil perioxidase assay. Its use as an assay for eosinophil differentiation factors. J. Immunol. Methods 83:209, 1985.

30. Hirano T., Matsuda T., Hosoi K., Okano A., Matsui H., Kishimoto T.: Receptor for B cell stimulatory factor 2(BSF-2): quantitative specificity, distribution and regulation of the expression. J. Exp. Med. 166:967, 1988.

31. Pelus L. M., Ottmann O. G., Nocka K. H.: Synergistic inhibition of human marrow granulocyte-macrophage progenitor cells by prostaglandin E and recombinant interferon-$\alpha$,-$\beta$, and-$\gamma$ and an effect mediated by tumor necrosis factor. J. Immunol. 140:479, 1988.

32. Lea T., Vartdal F., Davies C., Ugelstad J.: Magnetic monosized polymer particles for fast and specific fractionation of human mononuclear cells. Scand. J. Immunol. 22:207, 1985.

33. Civin C. I., Strauss L. C., Brovall C., Fackler M. J., Schwartz J. F., Shaper J. H.: Antigenic analysis of hematopoiesis. III. A hematopoietic cell surface antigen defined by a monoclonal antibody raised against KG-1a cells. J. Immunol. 133:157, 1984.

34. Hanson C. A., Gajl-Peczalska K. J., Parkin J. L., Brunning R. D.: Immunophenotyping of acute myeloid leukemia using monoclonal antibodies and the alkaline phosphatase-antialkaline phosphatase technique. Blood 70:83, 1987.

35. Warren D. J., Moore M. A. S.: Synergism among interleukin 1, interleukin 3 and interleukin 5 in the production of eosinophils from primitive hemopoietic stem cells. J. Immunol. 140:94, 1988.

36. McDonald T. P., Clift R., Lange R. D., Nolan C., Tribby I. I. E., Barlow G. H.: Thrombopoietin production by human embryonic kidney cells in culture. J. Lab. Clin. Med. 85:59, 1975.

37. Petursson S. R., Chervenick P. A.: Comparative effects of thrombopoietic-stimulatory factor and spleen cell conditioned medium on megakaryocytopoiesis in a short-term bone marrow liquid culture system. Exp. Hematol. 16:660, 1988.

38. Sparrow R. L., Oon S. H., Williams N.: Haemopoietic factors stimulating murine megakaryocytopoiesis: interleukin-3 is immunologically distinct from megakaryocyte-potentiator. Leuk. Res. 11:31, 1987.

39. Vainchenker W., Bouget J., Guichard J., Breton-Gorius J.: Megakaryocyte colony formation from human bone marrow precursors. Blood 54:940, 1979.

40. Dukes P. P., Egrie J. C., Strickland T. W., Browne J. K., Lin F.-K.: Megakaryocyte colony stimulating activity of recombinant human and monkey erythropoietin. In Levin R. F., Williams N., Levin J., Evatt B. L.(ed): Megakaryocyte Development and Function, Alan R. Liss, New York, 1986, p. 105.

41. Hoffman R. Straneva J., Yang H., Bruno E., Brandt J.: New insight into the regulation of human megakaryocytopoiesis. Blood Cell 13:75, 1987.
42. Peschel C., Paul W. E., Ohara J., Green I.: Effect of B cell stimulatory factor-1/interleukin 4 on hematopoietic progenitor cells. Blood 70:254, 1987.

What is claimed is:

1. A method of increasing megakaryocyte production in a mammal comprising administering a pharmaceutically effective amount of G-CSF and a pharmaceutically effective amount of G-CSF.

2. A method as in claim 1 wherein the G-CSF is administered simultaneously with GM-CSF administration or after GM-CSF administration.

3. A method as in claim 1 further comprising administration pharmaceutically effective amount of IL-6.

4. A method as in claim wherein 3 the IL-6 is administering from 0–7 days after G-CSF administration.

5. A method of increasing megakaryocyte production in a mammal comprising administering a pharmaceutically effective amount of IL-5 and a pharmaceutically effective amount of GM-CSF.

6. A method as in claim 5 wherein the IL-5 is administered simultaneously with GM-CSF administration or after GM-CSF administration.

7. A method of increasing blood platelets in a mammal comprising administering a pharmaceutically effective amount of IL-6 and a pharmaceutically effective amount of G-CSF or GM-CSF.

8. A method for the treatment of thrombocytopenia in a mammal comprising administering a pharmaceutically effective amount OF G-CSF and a pharmaceutically effective amount of GM-CSF.

9. A method as in claim 8 wherein G-CSF is administered simultaneously with GM-CSF administration or after GM-CSF administration.

10. A method as in claim 8 further comprising administering a pharmaceutically effective amount of IL-6.

11. A method as in claim 10 wherein IL-6 is administered from 0–7 days after G-CSF administration.

12. A method for the treatment of thrombocytopenia in a mammal comprising administering a pharmaceutically effective amount of IL-5 and a pharmaceutically effective amount of GM-CSF.

13. A method as in claim 12 wherein the IL-5 is administered simultaneously with GM-CSF administration or just after GM-CSF administration.

14. A method for the treatment of thrombocytopenia in a mammal comprising administering a pharmaceutically effective amount of IL-6 and a pharmaceutically effective amount of G-CSF or GM-CSF.

15. A method as in claims 8 or 14 wherein thrombocytopenia results from chemotherapy, radiation therapy or idiopathic thrombocytopenia purpura.

* * * * *